United States Patent

Weckström

[11] Patent Number: 5,900,635
[45] Date of Patent: * May 4, 1999

[54] CORRECTION OF COLLISION BROADENING IN NON-DISPERSIVE ABSORPTION MEASUREMENT OF GASES

[75] Inventor: Kurt Peter Weckström, Espoo, Finland

[73] Assignee: Instrumentarium Oy, Helsinki, Finland

[ * ] Notice: This patent issued on a continued prosecution application filed under 37 CFR 1.53(d), and is subject to the twenty year patent term provisions of 35 U.S.C. 154(a)(2).

[21] Appl. No.: 08/544,663

[22] Filed: Oct. 18, 1995

[30] Foreign Application Priority Data

Sep. 29, 1995 [FI] Finland .................................. 954632

[51] Int. Cl.⁶ .......................... G01N 21/61; G01N 21/35
[52] U.S. Cl. .......................... 250/345; 250/343; 356/437; 600/532
[58] Field of Search .................................. 250/345, 343; 128/719; 356/437; 600/532

[56] References Cited

U.S. PATENT DOCUMENTS

| | | | |
|---|---|---|---|
| 3,770,974 | 11/1973 | Fertig | 250/345 |
| 3,860,344 | 1/1975 | Garfunkel | 250/339 |
| 3,878,107 | 4/1975 | Pembrook et al. | 250/343 |
| 3,904,880 | 9/1975 | Benz et al. | 250/343 |
| 4,110,619 | 8/1978 | Zorner | 250/344 |
| 4,794,255 | 12/1988 | Miyatake et al. | 250/345 |
| 4,885,469 | 12/1989 | Yamagishi et al. | 250/345 |
| 5,036,198 | 7/1991 | Spaeth | 250/343 |
| 5,055,688 | 10/1991 | Fabinski | 250/343 |
| 5,077,469 | 12/1991 | Fabinski et al. | 250/345 |
| 5,332,901 | 7/1994 | Eckles et al. | 250/343 X |
| 5,464,982 | 11/1995 | Drucker et al. | 250/345 |
| 5,479,019 | 12/1995 | Gross | 250/345 |
| 5,486,699 | 1/1996 | Fabinski et al. | 250/345 |

FOREIGN PATENT DOCUMENTS

| | | |
|---|---|---|
| 349839 | 1/1990 | European Pat. Off. . |
| 29 09 688 | 9/1980 | Germany . |
| 55-152441 | 11/1980 | Japan .................................. 250/345 |
| 1-174943 | 7/1989 | Japan .................................. 250/345 |
| 1-74944 | 7/1989 | Japan .................................. 250/345 |
| 2113833 | 8/1983 | United Kingdom . |
| 2218804 | 11/1989 | United Kingdom . |

OTHER PUBLICATIONS

C. Cousin, R. Le Doucen, J.P. Houdeau, C. Boulet, and A. Henry, Air broadened linewidths, intensities, and spectral line shapes for $Co_2$ at 4.3 $\mu$m in the region of the AMTS instrument, Applied Optics, vol. 25, No. 14, Jul. 15, 1986.

Primary Examiner—Constantine Hannaher
Attorney, Agent, or Firm—Andrus, Sceales, Starke, & Sawall

[57] ABSTRACT

A method of non-dispersive analysis of gas mixtures for determining the concentration of some gas component therein. A radiation source is arranged which emits, through the gas mixture being analyzed, radiation within a wavelength range within which the absorption spectrum band used in the determination of the concentration of the said gas component is located; an optical transmission band filter the transmission band of which coincides with the said spectrum band is provided in the path of the radiation traversing the gas mixture being analyzed; a detector is used for detecting the radiation which has traversed the gas mixture being analyzed and the optical transmission band filter, whereby a first signal is obtained from the detector; a different second signal is generated in the detector by means of an additional gas or an additional gas mixture interposed between the radiation source and the detector; and the result of the concentration measurement is formed computationally by using the different measurement signals. Furthermore, in the method the transmission bands of the said transmission band filters are arranged within the same measuring range; as the additional gas there is used a compensation gas or a compensation gas mixture in which the compensation gas is the gas component the concentration of which is being determined or a corresponding other gas or a compensation filter. The absorption properties of the compensation filter are selected to be such, or the amount of the compensation gas is selected to be such, that the broadening of the absorption lines in the absorption spectrum band used will change the said different second signal.

27 Claims, 6 Drawing Sheets

CORRECTION OF COLLISION BROADENING IN NON-DISPERSIVE ABSORPTION MEASUREMENT OF GASES

BACKGROUND OF THE INVENTION

The invention relates to a method of non-dispersive analysis of gas mixtures for the determination of the concentration of a gas component present therein, the method comprising the following steps; a radiation source is arranged which emits, through the gas mixture being analyzed, radiation within a wavelength range within which the absorption spectrum band used in the determination of the concentration of the said gas component is located; an optical transmission band filter the transmission band of which coincides with the said spectrum band is provided in the path of the radiation traversing the gas mixture being analyzed; a detector is used for detecting the radiation which has traversed the gas mixture being analyzed and the optical transmission band filter, this first intensity generating in the detector a first signal; at least one different intensity is produced in the detector by means of an additional gas or an additional gas mixture interposed between the radiation source and the detector, by using radiation which has also traversed the gas mixture being analyzed and the transmission band filter, this second intensity generating in the detector a second signal; the result of the concentration measurement is formed computationally by using the different measurement signals. The invention also relates to the use of this method and to a sensor means used in its application.

In measuring the concentration of a gas by the infrared technique, the method most commonly used is a non-dispersive method, i.e. the absorption signal is measured through an optical transmission band filter having a transmission bandwidth typically in the same order of magnitude as the width of the spectrum band used for measuring the concentration of the gas component being measured. The measured radiation signal is in this case the integrated value of the transmissions at the different wavelengths of the transmission band. Such devices are described in publications U.S. Pat. No. 3,745,349 and HEWLETT-PACKARD JOURNAL, September 1981, pp. 3–5: R. J. Solomon—"A Reliable, Accurate $CO_2$ Analyzer for Medical Use." In the former publication, two infrared radiation sources emitting through the sample gas are used, but the radiation from one radiation source is rendered, for example by means of an optical gas filter, narrower than the wavelength range used in the measurement. The purpose is to provide a reference source issuing a radiation intensity which is not affected by the gas mixture being analyzed in the detector. The objective is to compensate for the effect of dirt and other substances accumulating in the measuring chamber and having absorption within the same range as the gas being measured, and to avoid the problems of matching different detectors. Modulated infrared sources are used, in which case an actual signal and a reference signal are obtained alternately in one and the same detector, signals which have thus traversed the same path and detect impurities in the same manner. In the former publication these problems have been solved by using a structure having no moving parts. In the latter publication, an attempt has been made to overcome the same problems but by using a rotating disk which contains different filters for obtaining a reference value.

The absorption spectrum of a gas in molecular form normally consists of absorption spectrum bands produced by molecular vibrations and, within them, a fine structure, i.e. absorption lines, due to rotational transitions. When measured with sufficient discrimination, the absorption spectrum band of a gas is thus made up of a large number of very narrow absorption lines. For example, carbon dioxide has a molecular vibration absorption spectrum band having a mean wavelength of 4260 nm. A more detailed analysis shows that the region is made up of more than 80 narrow absorption lines caused by rotation. The half-intensity linewidth and intensity of these lines are dependent on many factors, such as temperature, self-absorption due to the long measuring path, and collisions by other molecules present in the gas mixture. In measurement signal compensation on the first two can in general easily be taken into account by measuring the temperature and the linearization effects due to the measurement geometry on the gas concerned. On the other hand, the change, sometimes significant, due to collisions by other gas components must be taken into account specifically in order to minimize concentration errors. Changes in the half-intensity linewidth of carbon dioxide in a nitrogen mixture and an oxygen mixture are described in the publication APPLIED OPTICS, Vol. 25, No. 14/1986 pp. 2434–2439. Cousin, Le Doucen, Houdeau, Boulet, Henry—"Air broadened linewidths, intensities, and spectral line shapes for $CO_2$ at 4.3 $\mu$m in the region of the AMTS instrument." The half-intensity linewidth of the carbon dioxide line (ordinal number 67) of a gas mixture at normal pressure is, in an oxygen mixture, 0.055 cm$^{-1}$ (0.10 nm) and, in a nitrogen mixture, 0.060 cm$^{-1}$ (0.11 nm) for a concentration of 5% $CO_2$. The portion of self-broadening by carbon dioxide in these figures is only approx. 0.003 cm$^{-1}$.

Polar gases such as nitrous oxide have a much greater effect on the half-intensity linewidth than nitrogen and oxygen, discussed in the above-mentioned publication. For this reason, for example, the measurement result of the amount of carbon dioxide in a patient's breathing gas is corrected, for example, by measuring the laughing gas concentration, as in publication U.S. Pat. No. 4,423,739 and by using this result computationally to correct the carbon dioxide concentration. This method is not very reliable, for according to it, it is necessary to know, for example, all the gas components affecting the broadening of the absorption lines, their concentrations must be measured, and ample experimental material must be obtained for the correction calculations. The procedure described in the publication yields a completely erroneous result if there is some factor unknown in advance relating to the gas mixture being analyzed. It is known that the effect of oxygen on the measurement result of nitrogen can be corrected in a manner similar to that mentioned in the said patent, although the error is smaller. By the procedures described in publication U.S. Pat. No. 3,745,349 and in the said article in publication HEWLETT-PACKARD JOURNAL the problem described above cannot be solved, and it has not been discussed in them.

The concentration of a gas is proportional to the number of gas molecules at the measurement volume and pressure. The number of molecules participating in infrared absorption is retained more or less unchanged in a collision process if the conditions do not otherwise change. Only the distribution of energy is slightly changed, causing a broadening of the absorption line. The absorbance value integrated across the absorption line is thus retained practically unchanged. However, by the infrared technique it is not possible to measure absorbance directly; instead, transmission is measured. According to the Lambert-Beer law, $$T=10^{-s}$$

where T is transmission and a is absorbance, applies to one wavelength. Only linearization yields an absorbance value proportional to the concentration:

$$a = -\log T.$$

Especially when the measuring is carried out non-dispersively within a certain bandwidth, the total transmission signal Tm will be an integral across the spectrum range of the filter $\lambda 1-\lambda 2$:

$$Tm = \int_{\lambda 1}^{\lambda 2} F(\lambda) \cdot T(\lambda) d\lambda.$$

where $F(\lambda)$ is the wavelength-dependent transmission function of the filter and $T(\lambda)$ is the wavelength-dependent transmission function of the gas sample. This signal is linearized experimentally, since the Lambert-Beer law no longer applies. The end result is usually different from the total absorbance A, which is in practice independent of collision broadening and is an integral across absorbances $a(\lambda)$:

$$A = \int_{\lambda 1}^{\lambda 2} F(\lambda) \cdot a(\lambda) d\lambda.$$

In fact, the size of the error in Tm depends on the bandwidth of the filter. Measured by using a very narrow transmission band watch is in the same order as the total width (e.g. in the order of 0.1–1.5 nm) of an individual absorption line in the absorption band, the need for correcting the collision broadening is very small or nil. On the other hand, if the transmission band of the filter is even narrower (e.g. less than approx. 0.05–0.5 nm) than the full width of a single absorption line being measured, collision broadening causes a reduction of the signal corresponding to the concentration, since the absorption peak becomes lower. Such a case is reported in publication WO-94/24528, in which one absorption peak of oxygen is measured by using a very narrow-band laser diode. In this case, however, the Lambert-Beer law applies with respect to the laser wavelength, and after linearization the absorbance can be integrated as a function of the wavelength, so that the collision broadening can be compensated for.

If the filter band extends over a plurality of absorption peaks, as is usual in the measuring of carbon dioxide, there is need for correction, since the concentration reading increases as the collision broadening increases. Thus the problem caused by the broadening of the absorption lines is not solved by the arrangement described in publication EP-405 841, wherein two detections are used of which one is approximately within one half of the absorption spectrum band and at a concentration deviating (either high and/or low) from the measuring range of the gas being measured, and the other one is within the other half of the absorption spectrum band and at the analyzed concentration of the gas being measured, the result concentration being calculated on the basis of these measurements. Thus, for example, when the question is of certain isotopes of carbon dioxide, the measurements are carried out through transmission band filters of which one has a band of 4.0–4.4 μm and the other one a band of 4.2–4.6 μm. It is known that the extreme limits of the spectrum band concerned are 3.5 μm and 4.7 μm, and thus it must be noted that each range contains a large but indefinite number of absorption lines, in which case the situation is not necessarily always under control. The concentration error is also affected by the length of the measuring channel, i.e. that dimension of the measuring chamber in which radiation traverses it. In the case of a short channel the need for compensation is smaller, whereas in the case of a longer channel, in which the absorption of the gas being measured has reduced the transmission to a substantially greater degree, the need for compensation can be considerable. In the measuring of carbon dioxide in a patient's breathing air, in which for example a considerable portion of the gas mixture may be nitrous oxide, i.e. laughing gas, a concentration value measured and calculated in a conventional manner may be up to 15% too high, owing to the error explained above, due to the transmission integral.

BRIEF SUMMARY OF THE INVENTION

It is therefore an object of the present invention to provide a method and device for compensating for the above-described error due to the broadening of absorption lines in a normal non-dispersive gas measuring system wherein the width of the transmission band of the optical transmission band filter is greater than the width of an absorption line contained in the spectrum band of the gas being measured. A second object of the invention is such a method and device wherein it is possible, when so desired, to use for the measuring of a concentration a transmission band filter in which the width of the transmission band is at least equal to the width of the absorption spectra band of the gas concerned, but may thus be even considerably narrower. A third object of the invention is such a method and device in the use of which it is not necessary to identify the gas and/or measure the concentration of the gas which causes this broadening. It is also an object to eliminate, if possible, any other factors causing broadening, without their separate measuring and without correcting calculations based on experiments. A fourth object as of the invention is such a method and device which would be maximally simple and reliable in operation. A fifth object of the invention is such a method suited for the analysis of breathing air.

The disadvantages described above are eliminated and the objects defined above are attained by the method according to the invention, which is characterized in what is stated in the pertinent claims, and by means of the device according to the invention, which is characterized in what is stated in the pertinent claims.

In the method and device of the invention, an optical gas filter is used usually in addition to a wide-band filter, and a signal is generated which can be used for compensating for errors due to collision broadening of the absorption lines, regardless of the type of the ingredient gas causing the broadening. On the other hand, by a suitable selection of the parameters, it is also possible to develop a measuring method which automatically Measures a gas concentration correctly, regardless of any broadening of the absorption lines. There is thus no need to measure the concentrations of all the effective gases to clarify the need for compensation even if different gases have different effects on the collision broadening.

BRIEF DESCRIPTION OF THE SEVERAL VIEWS OF THE DRAWING

The invention is described below in detail, with reference to the accompanying figures.

DETAILED DESCRIPTION OF THE INVENTION

Figure 1A:
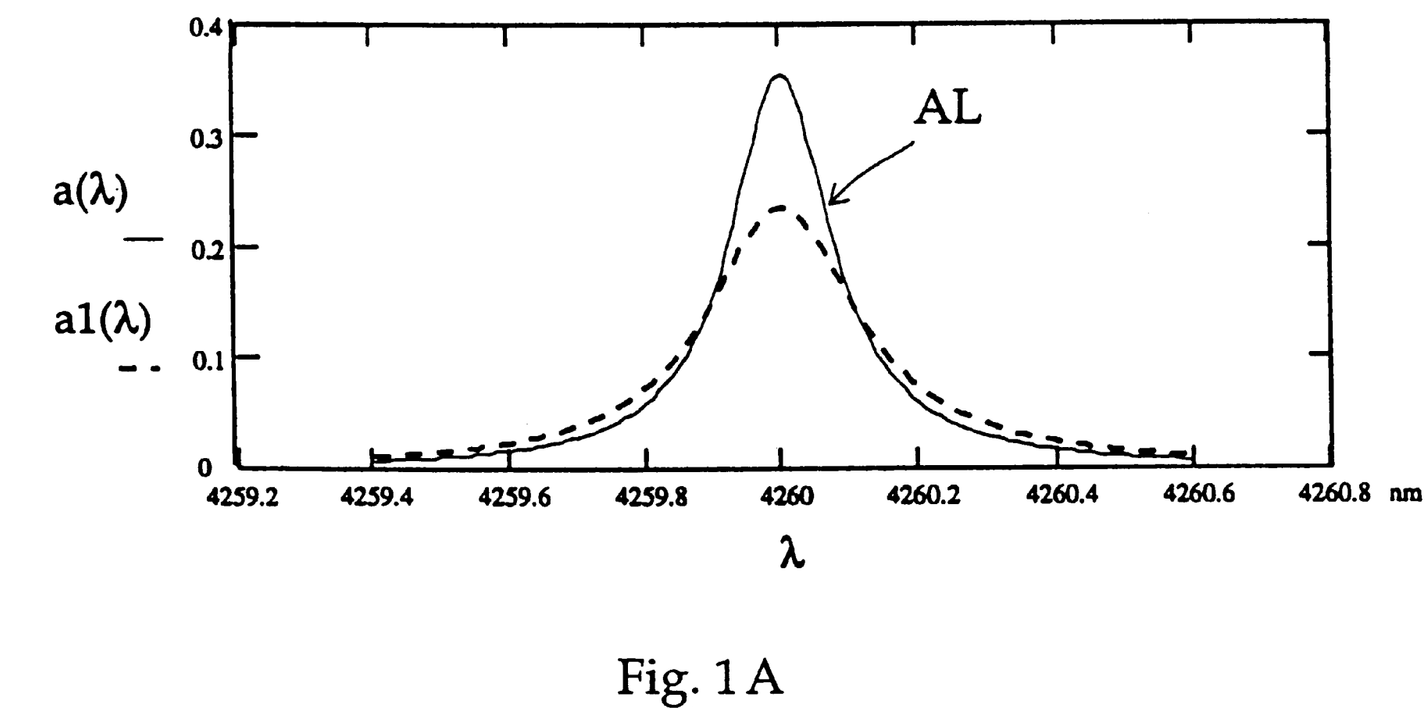
FIG. 1A depicts, in absorbance form, the behavior of one absorption line in one absorption spectrum band of carbon dioxide, the vertical axis representing the absorbance and the horizontal axis the wavelength, and the non-broadened form of the absorption line being shown with a solid curve and the form broadened under the effect of an ingredient gas being shown with a dashed curve.
Figure 1B:
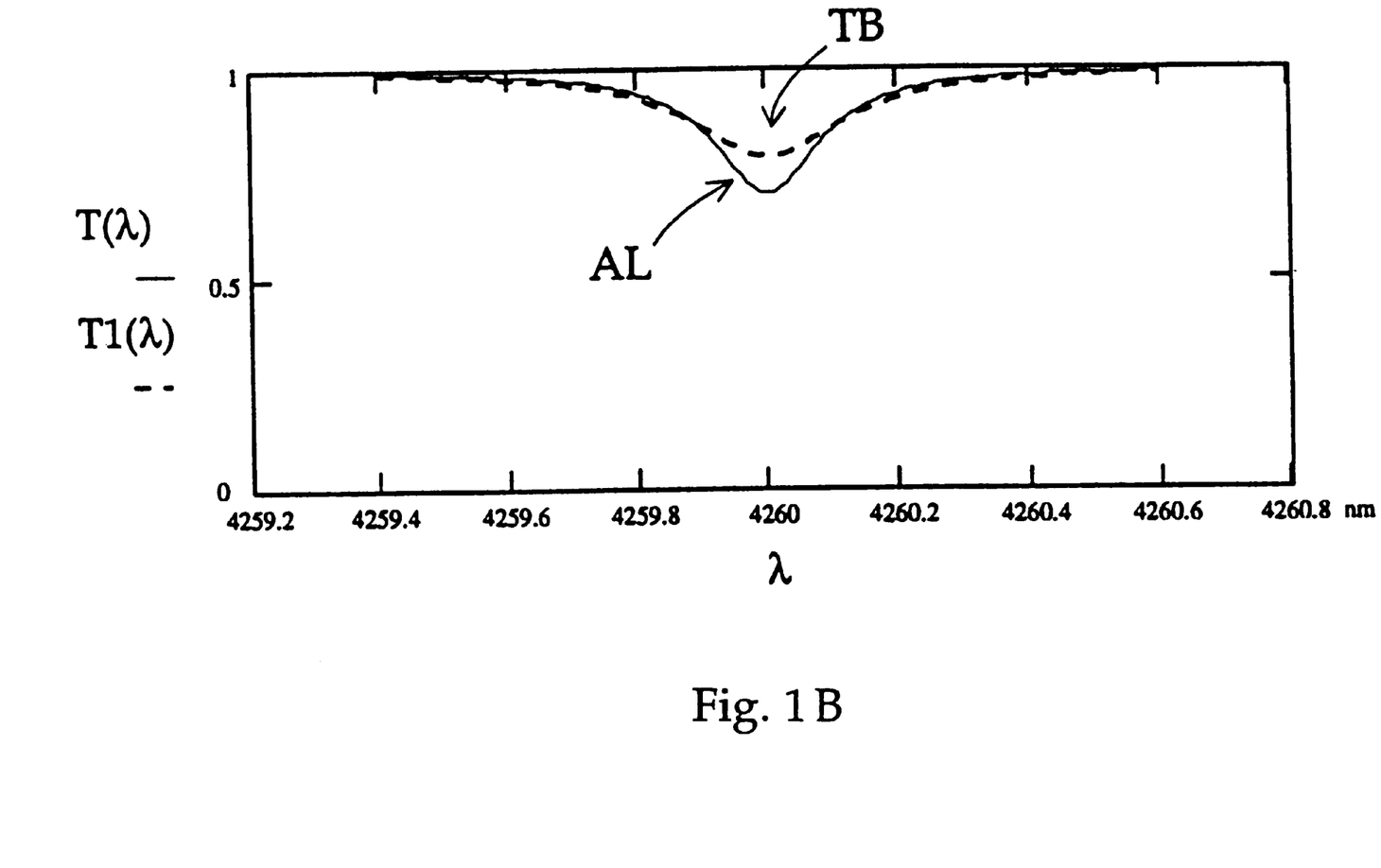
FIG. 1B depicts, in transmission form, the behavior of one absorption line in one absorption spectra band of carbon dioxide, the vertical axis representing the transmission and the horizontal axis the wavelength, and the non-broadened form of the absorption line being shown with a solid curve and the form broadened under the effect of an ingredient gas being shown with a dashed curve.
Figure 2:
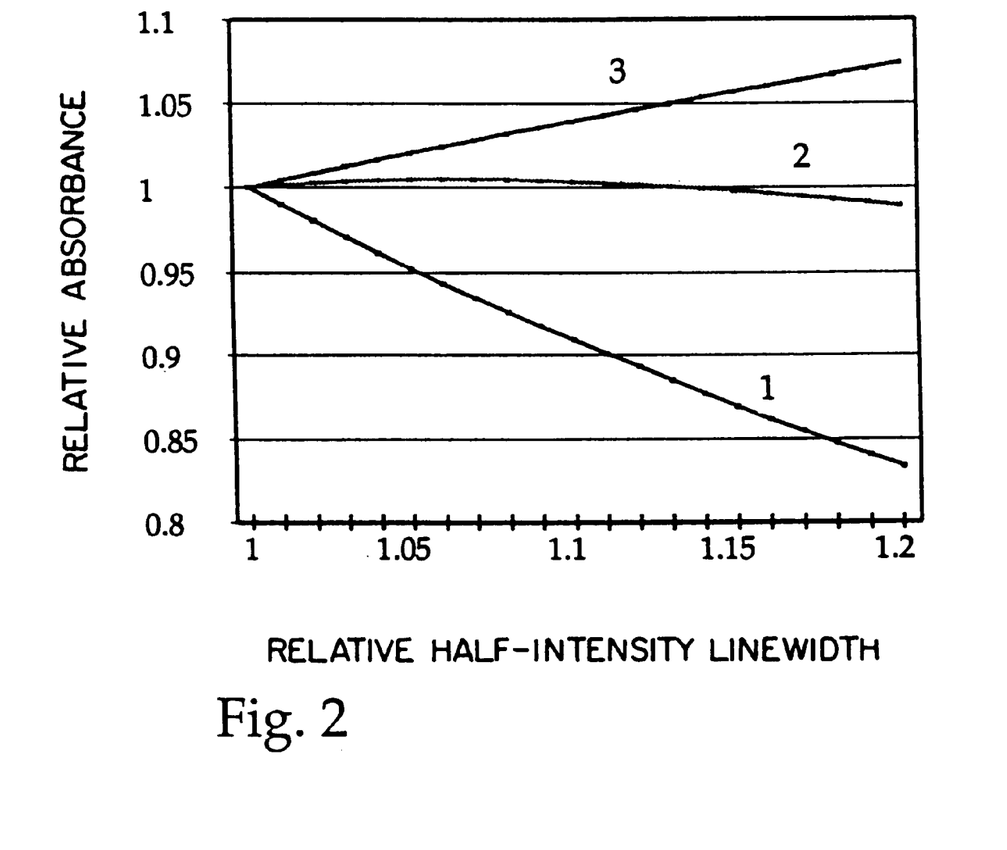
FIG. 2 depicts the effect of the width of the transmission band of an optical transmission band filter on the measurement signal with absorption line broadening of different magnitudes, the vertical axis representing the relative absorbance calculated from the measurement signal and the horizontal axis the relative half-intensity linewidth of the absorption line, the value of the half-intensity linewidth of a non-broadened absorption line being 1.

In order to make it possible to model approximately a real system for the measurement of a gas component in a gas mixture by using different widths of the transmission band of an optical transmission band filter, only one absorption line is examined, for example one rotation line AL belonging to the fine structure of the absorption spectrum band of carbon dioxide $CO_2$. In FIG. 1A such an absorption line AL is depicted as a function of the wavelength $\lambda$(nm) and as absorbance $a(\lambda)$ and $a1(\lambda)$, proportional to the concentration, for two different half-intensity linewidths (solid curve 0.1 nm and dashed curve 0.15 nm). In FIG. 1B the same absorption line AL is depicted as a function of the wavelength $\lambda$(nm) and as concentration-dependent transmission $T(\lambda)$ and $T1(\lambda)$, detected by the measuring system, for two different half-intensity line-widths of the absorption line (solid curve 0.1 nm and dashed curve 0.15 nm). As can be seen in FIG. 1A, the peak of the absorption line AL becomes lower as the line width increases, but in such a manner that the total area of the absorption line AL remains unchanged. Although it is not seen easily in FIG. 1B, the area of the transmission band TB detected by the measuring system increases as the absorption line broadens. In FIG. 1A the absorption line has been modeled by using the Lorentz function. It is assumed that the transmission band TB in FIG. 1B is measured using an optical transmission band filter having an ideal transmission band, in other words the edges of the band are sharp and the transmission is 100%. In this case the expected measurement signal for the various widths of the transmission band of the filter is easy to calculate. The result is shown in FIG. 2, which shows the linearized and normalized signal (i.e. the normalized absorbance value) as a function of the width, i.e. collision broadening, of the absorption line. The broadening is indicated as a relative value, the half-intensity linewidth of the non-broadened line having an arbitrary value of 1, and the absorbance is also presented as a relative value, starting from an arbitrary value of 1 when the absorption line AL is non-broadened. A relative value of 0.1 (=0.1*half-intensity linewidth) has been used as the width of the transmission band of a very narrow band filter, and the behavior of the calculated absorbance is seen in curve 1. As can be seen, the calculated absorbance value decreases as the width of the absorption line increases. If the bandwidth of the filter is selected suitably as in curve 2, in which the relative width of the filter transmission band is 1.8 (=1.8*half-intensity linewidth), the calculated absorbance value is almost independent of the broadening of the absorption line. Curve 3 shows the most common case, in which the transmission band of the filter is clearly wider than the width of one absorption line; in this example the value of the width is 4 (=4*half-intensity linewidth). It is thus an object of the invention to produce a signal, such as curve 2, which is independent of the broadening of the absorption line AL, by using a clearly wider band filter according to curve 3; according to the invention this is done surprisingly by simple new methods.

Figure 4A:
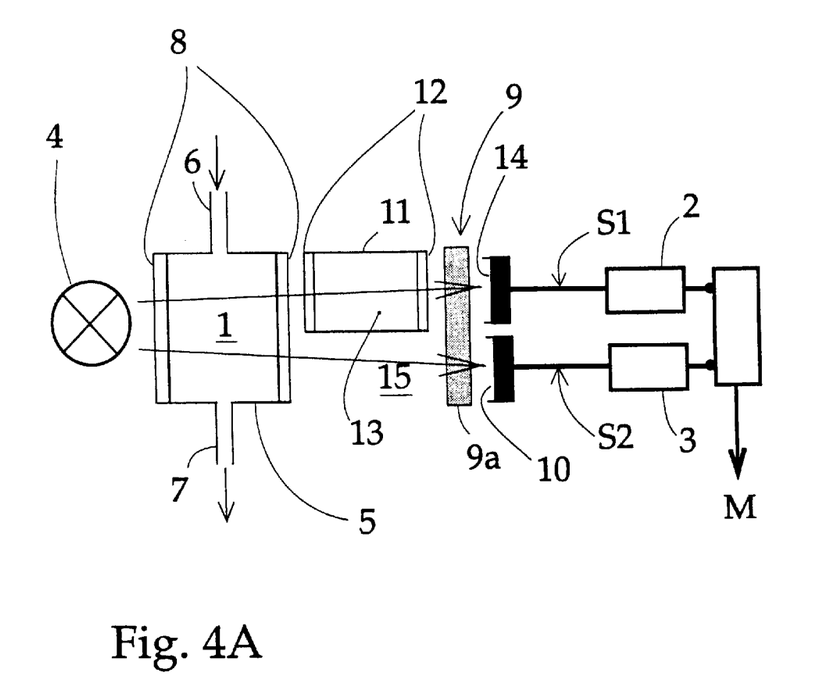
FIGS. 4A and 4B depict preferred first and second embodiments of the device according to the invention for generating a signal required for compensating for broadening of the absorption lines, in which embodiments the measurement signal and the compensation signal are obtained by means of one radiation source simultaneously, into parallel channels for joint data processing.
Figure 4B:
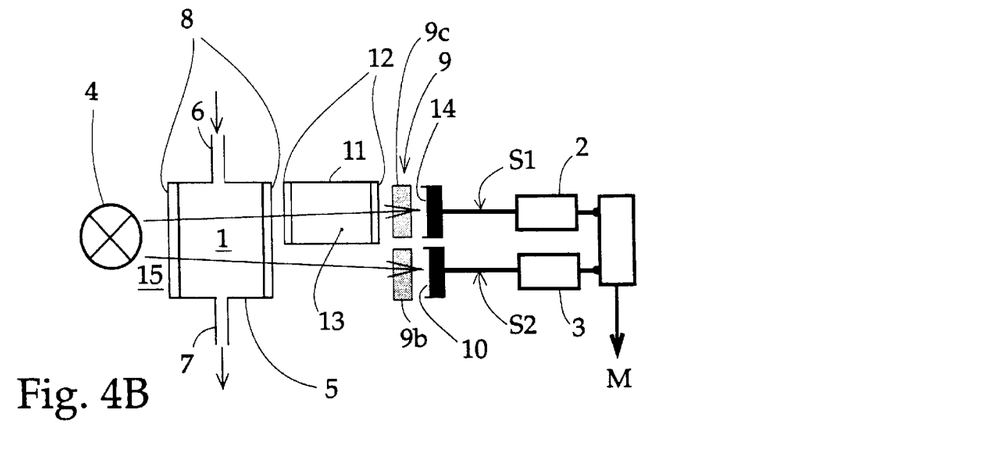

FIGS. 4A–4B, 5A–5B and 6 depict schematically measuring arrangements by means of which the signal required for compensating for collision broadening of the absorption line can be generated. In these embodiments, the same reference numerals or other reference markings are used for the same or analogous parts. FIGS. 4A and 4B show cases of a dual-channel measuring system for the measuring of infrared absorption, and thereby the concentration of a gas component. Although the system may be different in structure, as will be described below, the principle of measuring in accordance with the invention is highly evident from the system depicted in FIG. 4A. The radiation source 4 is in general common to both measuring channels 2, 3 in order that any variation in radiation 15 should be the same in both channels. The sample cheer 5 is also preferably common in order that, for example, time delays should be avoided. An inlet pipe 6 and outlet pipe 7 for the sample gas are linked to the sample chamber 5, and the chamber has windows B permeable to radiation. Along this path the gas mixture 1 being analyzed, from which the concentration of some gas component is being determined, can be caused to travel through the sample cheer. The gas mixture is typically a patient's breathing air, and the sample chamber 5 can be installed either as a mainstream sensor or, preferably, as a sidestream sensor.

The actual measuring channel 3 has an optical transmission band filter, which is generally indicated by 9, and a detector 10, from which an electrical signal S2 is obtained for further processing. The transmission band of the transmission band filter 9 is coincident with the desired absorption spectrum band of the gas component being measured. In the case of carbon dioxide, the middle point of this range is at wavelength 4.26 μm and its usable width is approx. 0.2 μm. As explained in the foregoing, more than 80 narrow absorption lines fit within this band. The transmission band of the filter 9 may be somewhat wider than the width of the absorption band, e.g. 0.25 μm, but typically it is approximately equal to the absorption bandwidth. The transmission band may also be narrower than the absorption bandwidth 0.2 μm, as long as it is, in the manner described above, substantially wider than the width of a single absorption line, i.e. more than approx. 0.4 nm. The absorbance value calculated from the signal S2 obtained from detector 10 in this case behaves in the manner shown by curve 3 in FIG. 2, i.e. the value calculated for the concentration of the gas becomes too high if the sample chamber contains, for example, laughing gas in addition to carbon dioxide.

According to the invention, the transmission band filter 9 in the compensation measuring channel 2 is preferably the same filter 9a as in the actual measuring channel 3. The transmission band filter in the compensation channel 2 may, of course, be a filter 9c different from the transmission band filter 9b in the actual measuring channel 3, as in the embodiment of FIG. 4B, as long as their transmission bands are at least approximately similar, Preferably the filters 9b and 9c in the different channels are maximally similar, i.e. which condition is easily fulfilled in the embodiment of FIG. 4A. In addition, this channel 2 has a compensation filter 11, in this case a gas container which has windows 12 permeable to the radiation concerned and the gas content 13 of which consists at least in part of the same gas as the goes being measured, in this case thus carbon dioxide. The pressure of the gas may, according to need, be other than normal pressure, and the gas may also be a gas mixture containing the gas type being measured, in which mixture the other components are preferably neutral, i.e. do not cause broadening of the absorption lines. The pressure of the gas or the gas mixture and/or the concentration of the gas component being measured, i.e. its volume proportion in the gas mixture and/or measuring length of the gas or the gas mixture (that dimension of the gas contained in the orientation of which the radiation 15 traverses it) is, according to the invention, arranged to be such that the broadening of the absorption lines in the absorption spectrum bared used will change the said different intensity and thereby the second signal S1. Any changing of the pressure, concentration and/or volume will change the number of gas component molecules incident on the path of the radiation 15 and will thereby affect the degree of broadening of the absorption lines. The signal S1 in electrical form is obtained from detector 14.

Figure 3:
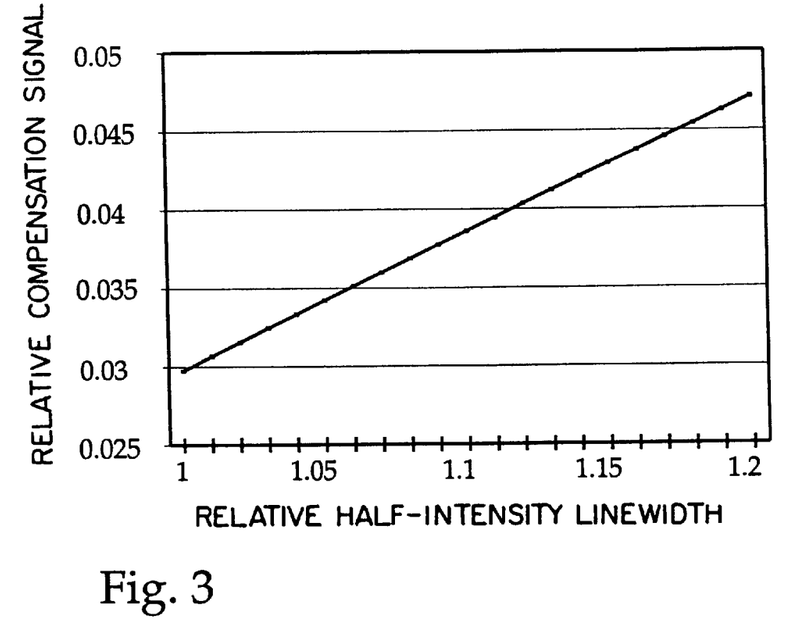
FIG. 3 depicts a theoretical collision broadening correction signal obtained by the method and measuring system according to the invention, the vertical axis representing the relative compensation signal and the horizontal axis the relative half-intensity linewidth of the absorption line, the value of the half-intensity linewidth of the non-broadened absorption line being 1, as in FIG. 2.

The compensation gas 13 in the gas container, which gas thus includes some of the gas type being measured, serves as an optical filter which filters the radiation 15 in the region of the absorption liner of the gas in the container. In the region of the wavelengths outside the absorption lines the radiation will travel without hindrance to detector 14. Detector 14 is thus not at all capable of detecting, or detects only slightly, the gas of the same type in the sample chamber 5, since the radiation in the region of the absorption lines of the said gas component being measured is filtered at least in part by the gas 13 in the container. Now, if the composition of the compensation gas 13 in the container is selected suitably, for example so that the width of the absorption lines of the compensation gas mixture is equal to the width of the absorption lines of the gas component being measured, or at least close to this width, in a situation in which the absorption lines of the gas component being measured are non-broadened, the detector 14 detects more absorption when the sample chamber 5 contains, in addition to the gas component being measured, also a gas such as laughing gas which broadens its absorption lines through the collisions discussed above. The signal S1 of detector 14 in this case thus contains information on the broadening of the absorption lines of the gas component being measured. If this signal is linearized mathematically (i.e. the absorbance is calculated), a signal, depicted for example in FIG. 3, dependent on the broadening of the absorption line of the gas component being measured is obtained, and it can, after suitable modification, be used for compensating for the signal obtained from detector 10. The curve shown in FIG. 3 has been calculated according to the modeling described above, as are the curves in FIG. 2, assuming that the half-intensity linewidth of the absorption lines of the compensation gas 13 in the gas container is approx. 1.2-fold the half-intensity linewidth of the non-broadened absorption lines. If the gas mixture or the length of the container or the pressure in the container is selected so that this half-intensity linewidth will be greater, the useful signal S1 obtained from detector 14 will decrease even if its dependence on the broadening is retained. Thus the half-intensity linewidth of the absorption lines of the compensation gas need no, necessarily have a relative value of 1, although this is preferable, as long as the half-intensity linewidth of the absorption lines of the compensation gas 13 is smaller than the half-intensity linewidth of the absorption lines of the gas being measured in the measuring situation, i.e. broadened. This result is thus achieved, for example, by using as the compensation gas 13 the gas being measured, unmixed, or the gas being measured in a mixture with gases not affecting the broadening of the absorption lines.

It has been described above how a signal S1 dependent on collision broadening can be used for measurement signal S2 compensation regardless of whether there is information available on the type and quantity of the gas causing the broadening. The measuring arrangement shown in FIGS. 4A–4B is, with certain qualifications, also suitable for automatic compensation for collision broadening. It is possible to imitate the situation of curve 2 in FIG. 2, in which measuring is carried out by using an optical filter or radiation having a bandwidth in the same order as the width of the absorption spectrum band of the gas being measured. If the components in the two measuring channels are identical and a suitable adjustment of the amplification coefficient is made in the signal of one channel, the difference between the signal S2 of detector 10 in the measuring channel 3 and signal S1 of detector 14 in the compensation channel 2 can be used as a compensated measurement signal from which the measurement result M can be calculated. Let us assume, for example, that the signal S2 obtained from detector 10 is in the order of magnitude of H. Since the compensation channel has a container containing the gas type 13 being measured or a corresponding compensation filter 11, the signal obtained from detector 14 is $S1=H-k*D$, where D is the width portion of the absorption lines of the absorption spectrum band of the gas and k is the absorbed portion of the transmission value of the transmission band filter 9 at the wavelengths concerned. The value of the coefficient k may be, for example, 0.8 if 80% of the radiation has been absorbed in the region of the gas absorption lines. If the sample chamber 5 contains no gas being measured, the reference value obtained for the compensated signal M will be the difference between detector 10 and detector 14, i.e. $k*D$. When gas being measured enters the sample chamber 5, it will absorb a portion d of the signals of both detector 10 and detector 14 within a wavelength width portion of approximately D. The signal of detect or 10 is now $S2=R-$ d*D and the signal of detector 14 is S1=H−k*D−(1−k)*d*D, in which case the difference is k*D*(1−d). When this is normalized mathematically by dividing it by the value k*D, the value 1−d is obtained for the transmission signal. This result is the same as it would be if filter 9 had been a filter in accordance with the widths of the absorption lines. In that case, without a gas being measured in the chamber 5 the signal would have been, for exile, k*D and with a gas being measured it would have been (1−d)*k*D, from which value 1−d is also obtained as transmission. By a suitable selection of the composition of the gas 13 in the gas container, or alternatively the properties of the filter 11, it is thus possible to simulate a situation in which the measurement signal is not dependent on the collision broadening of the gas being measured present in the sample chamber 5, as shown by curve 2 in FIG. 2.

In a general form the above calculation and deduction can be defined in words in the following manner. The said amount of the compensation gas 13 in the container which constitutes the compensation filter is set at such a value that detector 14 will receive an intensity which decreases as the broadening of the absorption lines contained in the absorption spectrum band of the gas component being measured increases. This reduces the compensation signal S1 obtained from the detector and increases the absorbance value obtained from it. When, in the manner described above, the widths of the transmission bands of both transmission band filters 9 are arranged to be greater than the width of one or more absorption lines belonging to the absorption spectrum band being used and to function usually within the same measuring range and to be typically identical but narrower than the distance between those edges of adjacent absorption spectrum bands which are closest to each other, detector 10 will receive an intensity which decreases as the broadening of the absorption lines contained in the absorption spectrum band increases, which will reduce the measurement signal S2 obtained from this detector. Here it should be noted in particular that the absorbances change in a direction opposite to that in which the intensities change as the absorption lines broaden. By the same measuring range is meant here that the transmission bands are at least in the main within the same wavelength range, in which case they may thus advantageously be of the same width and coincident, or they may deviate in width, thus being one within the other. However, it is not advantageous for the transmission bands to overlap with respect to wavelengths, in which case they will have transmissions deviating from each other, although this can also be done. The final measurement signal M is obtained computationally by using signals S1 and S2. The amount of the compensation gas must be selected so that the detector 14 will receive a low intensity when the radiation arrives from the radiation source through the compensation gas, through the gas being analyzed which contains the mean expected concentration of the gas component being measured, and through the transmission band filter. According to present knowledge, this low intensity arriving at detector 14 will be at least 0.01% and at most 50%, possibly within 0.1–5%, of the intensity arriving at detector 10 when no substantial broadening of the absorption lines occurs in the gas being analyzed.

Figure 5A:
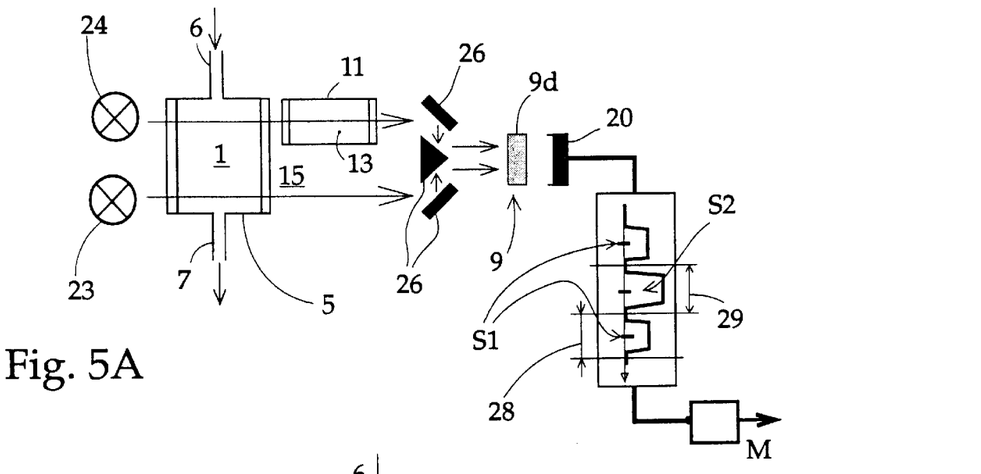
FIGS. 5A and 5B depict third and fourth embodiments of the device according to the invention for generating a signal required for compensating for broadening of the absorption lines, in which embodiments the measurement signal and the compensation signal are obtained by using two radiation sources, in successive the periods, into one channel for joint data processing.
Figure 5B:
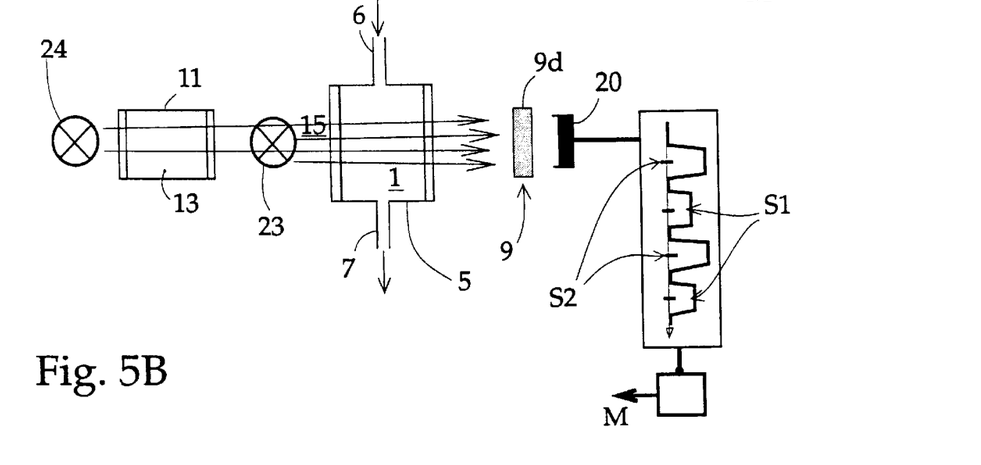

FIGS. 5A and 5B depict arrangements corresponding in other respects, but in them there are used two radiation sources 23, 24 and one transmission band filter 9d and one detector 20, which is directed towards both radiation sources. The radiation from one radiation source 23 traverses only the gas mixture L being analyzed and the radiation from the other radiation source 24 additionally traverses the compensation gas 13 in a container constituting the compensation filter 11. Thus a measurement signal S2 and a compensation signal S1, quite corresponding to what was described above, are obtained Since the arrangement has only one detector, the radiation sources 23, 24 are modulated, whereby one set of time periods 28 are generated for the compensation signal S1 and another set of time periods 29 for the measurement signal S2, these time periods 28, 29 alternating, in which case the signals S1, S2 are obtained as successive pulses or the like. In this case, also, the amount of the compensation gas 13 and the transmission band of the transmission hand filter 9 are set in accordance with the principles of the invention, described above. The embodiments of FIGS. 5A and 5B differ only with respect to the placement of the components, with the exception that FIG. 5A has mirrors 26 or other similar means for collecting radiation 15.

Figure 6:
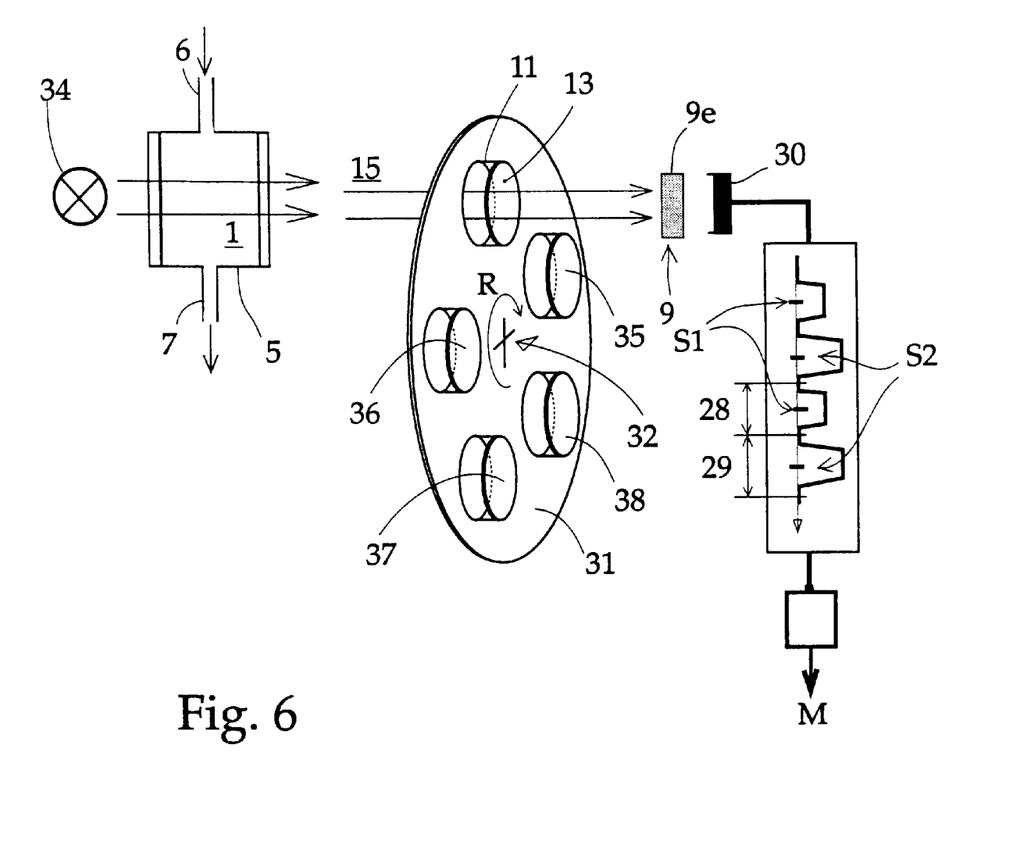
FIG. 6 depicts a fifth embodiment of the device according to the invention for generating a signal required for compensating for broadening of the absorption lines, in which embodiment the measurement signal and the compensation signal are obtained by means of one radiation source in successive time periods, into one channel for joint data processing.

FIG. 6 further shows a corresponding embodiment, using one radiation source 34 and one detector 30 which is directed towards the radiation source. A sample chamber 5 containing the gas mixture 1 being analyzed is interposed between the detector and the radiation source. Between the detector and the radiation source there is continuously, for example, a fixed transmission band filter 9e, which has the properties described above generally in connection with filter 9. Furthermore, the device has, between the detector and the radiation source, a filter disk 31, for example rotating in the direction R about axis 32, by means of which disk there is introduced into the path of the radiation 15 alternately a compensation gas 13 in a container constituting a compensation filter 11 according to the insertion, described above, and a non-absorbing medium. This non-absorbing medium may be air, which is simply provided by means a hole in the disk, or some other analogous gas or a vacuum or some other analogous medium. In this manner, successive time periods 28, 29 are formed, within which time periods both the first signal S2 and the second signal S1 are obtained as successive pulses or the like. In this case, also, the amount of the compensation gas 13 is set in accordance with the principles of the invention, described above. Reference numerals 36–38 indicate other possible filters or other reference gas containers or other compensation filters for other purposes.

In the method and device according to the invention, the radiation source 4, 23–24 and 34 is preferably an emitter emitting within a wide spectrum range, and thus typically a thermal emitter, in order that its emission should be relatively even, and preferably constant, within the whole width of the absorption spectrum band used. If only a portion of the whole width of the band is used for the measuring, i.e. only some of the absorption lines of the band, the radiation source may be even of some other type. However, lasers are not suitable, since their emission bands are typically narrower than a single absorption line, as was noted above. The transmission band filter 9a, 9b–c, 9d and 9e may be of any type suitable for the purpose, as long as its transmission band can be made so narrow that it is approximately of the width of the absorption spectrum line used, or narrower. Thus the transmission band filter is typically an interference filter produced by multi-layer coating, a so-called dichroic filter. The sensors 10–14, 20 and 30 may be of any type suitable for the purpose.

The absorption band of the compensation filter 11 according to the invention is made up of a large number of adjacent, separate absorption peaks, each of the peaks corresponding precisely to one absorption line of the gas component being measured Thus the absorption band of the filter is "comb-like", and in it the wavelengths of each absorption peak are substantially the same as the wavelengths of the corresponding absorption lines of the gas component being measured. The only difference is that in the compensation filter 11 the absorption peaks, i.e. the absorption lines in the case of a filter produced by using a compensation gas 13, are at least not substantially broadened and are constant in width, whereas the absorption lines of the gas component being measured, present in the sable chamber, may be broadened to a greater or lesser degree, depending on the accompanying gases, as was stated above. Such a compensation filter 11 is thus produced most simply by using a compensation gas 13 which is the same as the gas being measured. If, for example, only one absorption line is used in the measuring, in which case the transmission band of the transmission band filter 9 is wider than one line but smaller than the distance between the closest edges of adjacent lines, it is possible to use as the compensation filter 11, for example, a Fabry-Perot filter or a Fabry-Perot etalon, by means of which the transmission corresponding to one absorption line can be simulated. In theory it is conceivable that, if a plurality of adjacent absorption lines are used in the measuring, wherein the transmission band of the transmission band filter 9 is wider than the united width of these lines but smaller than the distance between the closest edges of the first lines not used, could the multiples of transmissions of Fabry-Perot filter or etalon be used as a compensation filter 11, each multiple of transmission simulating in each case the transmission of one absorption line. It is also conceivable, that some gas other than the gas being measured would have one or more absorption lines width sufficient precision the sane as sane absorption line of the gas being measured, in which case it can be used as a compensation gas 13.

The method according to the invention is especially suitable for measuring the concentration of carbon dioxide in a patient's breathing air, for example alveolar breathing air coming from deep in the lungs, since breathing air always, and in particular during surgical operations and anesthesia, contains substances which increase the width of absorption lines, the effect of which substances can easily be compensated for by means of the invention. There is no obstacle to the use of the method and devices according to the invention also for the determination of concentrations of other gases in the absorption spectrum bands of which the absorption lines broaden under the effect of, for example, other gas components.

For a person skilled in the art it is clear that the measuring arrangements depicted in the figure are not the only ones to which the compensation method according to the invention can be applied; in principle the method can be applied to any and all non-dispersive measuring systems which use an optical transmission band filter having a transmission bandwidth greater thaw the width of the absorption lines of the gas.

I claim:

1. A method for determining the concentration of a given gas in a mixture of gases by means of non-dispersive absorption of radiation, the method providing compensation for the effects of collision broadening of absorption lines in the absorption spectrum of the given gas, said method comprising the steps of:

(a) providing a sample of the gas mixture;
   (b) passing radiation through the gas mixture, the radiation having a wavelength range including an absorption spectrum band for determining the concentration of the given gas;
   (c) applying the radiation exiting the gas mixture to a first optical transmission band filter, the first filter having a transmission bandwidth selected from a range of bandwidth values having a maximum value substantially equal to the width of the absorption spectrum band and a minimum value less than the width of the absorption spectrum band;
   (d) detecting the intensity of the radiation transmitted through the first optical transmission band filter to provide a first signal, the detected radiation, and hence the first signal, being subject to the effects of collision broadening occurring from the mixture of gases;
   (e) providing a compensation filter, the compensation filter including a compensating gas including a known concentration of the given gas at a known pressure, any collision broadening effects occurring in the compensating gas usually differing from those occurring in the gas mixture;
   (f) passing radiation through both the gas mixture and the compensating gas;
   (g) applying the radiation passed through the gas mixture and compensating gas to a second optical transmission band filter, the second filter having a transmission bandwidth selected from a range of bandwidth values having a maximum value greater than the width of the absorption spectrum band and a minimum value less than the width of the absorption spectrum band;
   (h) detecting the intensity of the radiation transmitted through the second filter to provide a second signal, the detected radiation, and hence the second signal, being subject to the differing collision broadening effects resulting from passage through the compensating gas; and
   (i) providing an output from the first and second signals which is compensated for the effects of collision broadening in the absorption spectrum of the given gas and is, thus, an accurate determination of the concentration of the given gas in the gas mixture.

2. A method according to claim 1 wherein step (e) is further defined as providing a compensation filter with a compensating gas in which the absorption lines of the given gas are not substantially broadened and wherein the amount of compensating gas included in the compensation filter is such that the intensity of the radiation detected and second signal provided in step (h) decrease as the collision broadening of the absorption lines of the given gas in the gas mixture increases.

3. A method according to claim 1 wherein step (e) is further defined as providing a compensation filter in which the amount of compensating gas is such that the intensity of the radiation detected in step (h), when the gas mixture contains a mean expected concentration of the given gas, is in a range of 0.01% and to 50% of the radiation intensity detected at step (d) when no substantial broadening of the absorption lines of the given gas occurs in the gas mixture.

4. A method according to claim 1 wherein step (c) is further defined as applying the radiation to a first optical transmission band filter having a transmission bandwidth which is substantially equal to the width of the absorption spectrum band.

5. A method according to claim 1 wherein step (c) is further defined as applying the radiation to a first optical transmission band filter having a transmission bandwidth which is narrower than the width of the absorption spectrum band but substantially wider than the width of an absorption line.

6. A method according to claim 1 wherein step (c) and (g) are further defined as applying radiation to optical transmission band filters having the same transmission bandwidth.

7. A method according to claim 1 wherein steps (b) and (f) are further defined as passing radiation from a single radiation source and wherein the detecting in steps (d) and (h) are carried out simultaneously.

8. A method according to claim 1 wherein radiation passing steps (b) and (f) are further defined as being carried out on an alternating basis and wherein steps (d) and (h) are carried out to alternately provide signals.

9. A method according to claim 8 wherein steps (d) and (h) are carried out using a single detector.

10. A method according to claim 1 wherein steps (b) and (f) are further defined as passing radiation from a single radiation source, wherein steps (d) and (h) are carried out using a single detector, and wherein step (e) is further defined as providing and removing the compensation filter from a radiation path extending between the radiation source and the detector, the provision of signals in steps (d) and (h) occurring successively.

11. A method according to claim 1 further including the steps of amplifying the first and second signals by different amplification coefficients and wherein step (i) is further defined as using the difference between said first and second signals to provide the compensated output.

12. A method according to claim 1 further defined as a method for determining the concentration of a given gas comprising carbon dioxide in a gas mixture comprising the respiration air of a subject.

13. A method according to claim 12 further defined as a method for determining the concentration of carbon dioxide in a gas mixture comprising the alveolar exhalation air of the subject.

14. An apparatus for providing an indication of the concentration of a given gas in a mixture of gases, said apparatus employing non-dispersive absorption of radiation and providing an output compensated for the effects of collision broadening of absorption lines in the absorption spectrum of the given gas, said apparatus comprising:

a sample chamber containing the gas mixture;

a radiation source means providing radiation to first and second radiation paths in said apparatus, the radiation having a wavelength range including an absorption spectrum band for determining the concentration of the given gas, said sample chamber being located in said first and second paths so that radiation from said radiation source means passes through said sample chamber;

a first optical transmission band filter located in said first radiation path for receiving radiation passed through said sample chamber, said first filter having a transmission bandwidth selected from a range of bandwidth values having a maximum value substantially equal to the width of the absorption spectrum band and a minimum value less than the width of the absorption spectrum band;

a compensation filter means located in said second radiation path, the compensation filter means including a compensating gas including a known concentration of the given gas at a known pressure, any collision broadening effects occurring in the compensating gas as usually differing from those occurring in the gas mixture;

a second optical transmission band filter in said second radiation path for receiving the radiation passed through said sample chamber and compensation filter means, said second filter having a transmission bandwidth selected from a range of bandwidth values having a maximum value substantially equal to the width of the absorption spectrum band and a minimum value less than the width of the absorption spectrum band;

detector means for detecting the intensity of the radiation transmitted through said first filter to provide a first signal, the detected radiation, and hence the first signal, being subject to the effects of collision broadening occurring from the mixture of gases, said detector means further detecting the intensity of the radiation transmitted through said second filter to provide a second signal, the detected radiation, and hence the second signal, being subject to the differing collision broadening effects resulting from passage through the compensating gas; and means for applying the second signal to the first signal to provide an output which is compensated for the effects of collision broadening in the absorption spectrum of the given gas and is, thus, an accurate indication of the concentration of the given gas in the gas mixture.

15. An apparatus according to claim 14 wherein said compensation filter includes a compensating gas in which the absorption lines of the given gas are not substantially broadened and wherein the amount of compensating gas included in the compensation filter is such as to cause the intensity of the radiation detected and second signal provided by said detector means to decrease as the collision broadening of the absorption lines of the given gas in the gas mixture increases.

16. An apparatus according to claim 14 wherein said compensation filter includes an amount of compensating gas such that the intensity of the radiation detected by said detector means, when the gas mixture contains a mean expected concentration of the given gas, is in a range of 0.01% to 50% of the radiation intensity detected by said detector means when no substantial broadening of the absorption lines of the given gas occurs in the gas mixture.

17. An apparatus according to claim 14 wherein said first filter is further defined as having a transmission bandwidth which is substantially equal to the width of the absorption spectrum band.

18. An apparatus according to claim 14 wherein said first filter is further defined as having a transmission bandwidth which is narrower than the width of the absorption spectrum band but substantially wider than the width of an absorption line.

19. An apparatus according to claim 14 wherein said first and second filters have the same transmission bandwidth.

20. An apparatus according to claim 14 wherein said first and second filters comprise a single filter means.

21. An apparatus according to claim 14 wherein said radiation source means comprises a single radiation source.

22. An apparatus according to claim 14 wherein said radiation source means comprises a pair of radiation sources one of which provides radiation to said first radiation path, the other of which provides radiation to said second radiation path.

23. An apparatus according to claim 22 wherein said detector means comprises a first detector for said first radiation path and a second detector for said second radiation path.

24. An apparatus according to claim 14 wherein said first and second radiation paths are combined into a common radiation path extending from said radiation source means to said detector means, and wherein said compensation filter means is further defined as movable into and out of said common radiation path for providing said first and second signals from said detector means.

25. An apparatus according to claim 14 further including means for amplifying said first and second signals by different amplification coefficients and said applying means is further defined as using the difference between sand first and second signals to provide the compensated output.

26. An apparatus according to claim 14 further defined as an apparatus for providing an indication of the concentration of a given gas comprising carbon dioxide in a gas mixture comprising the respiration air of a subject.

27. An apparatus according to claim 26 further defined as an apparatus for providing an indication of the concentration of carbon dioxide in a gas mixture comprising the alveolar exhalation air of the subject.

* * * * *